United States Patent [19]

Shiratori et al.

[11] Patent Number: 5,211,879
[45] Date of Patent: May 18, 1993

[54] ESTER COMPOUNDS AND LIQUID CRYSTAL COMPOSITIONS CONTAINING THE SAME

[75] Inventors: Nobuyuki Shiratori; Isa Nishiyama; Atsushi Yoshizawa; Toshihiro Hirai, all of Toda, Japan

[73] Assignee: Nippon Mining Co., Ltd., Tokyo, Japan

[21] Appl. No.: 604,827

[22] Filed: Oct. 29, 1990

[30] Foreign Application Priority Data

Nov. 7, 1989 [JP] Japan .................................. 1-287994
Jan. 19, 1990 [JP] Japan ...................................... 2-8505
Apr. 13, 1990 [JP] Japan .................................... 2-96320

[51] Int. Cl.$^5$ ...................... C09K 19/20; C09K 19/34; C09K 19/12; C07C 69/76
[52] U.S. Cl. ............................ 252/299.67; 252/299.66; 252/299.61; 252/299.65; 560/65; 560/76; 560/102
[58] Field of Search ....................... 252/299.61, 299.66, 252/299.67; 560/65, 76, 102, 108

[56] References Cited

U.S. PATENT DOCUMENTS

| | | | |
|---|---|---|---|
| 4,874,545 | 10/1989 | Heppke et al. | 252/299.61 |
| 4,906,402 | 3/1990 | Jackson et al. | 252/299.65 |
| 4,999,130 | 3/1991 | Nohira et al. | 252/299.01 |
| 5,051,527 | 9/1991 | Suzuki et al. | 560/51 |
| 5,116,527 | 5/1992 | Coates et al. | 252/299.61 |

FOREIGN PATENT DOCUMENTS

0343487 11/1989 European Pat. Off. .
59-118644 7/1984 Japan .
61-43 1/1986 Japan .
61-165350 7/1986 Japan .
61-200973 9/1986 Japan .
64-3154 1/1989 Japan .

OTHER PUBLICATIONS

Chemical Abstracts, vol. 112, No. 12, Mar. 19, 1990, Columbus, Ohio, USA, S. Shungo et al., "Optically active fluoromethylmalonate esters and liquid crystal compositions".

*Primary Examiner*—Robert L. Stoll
*Assistant Examiner*—C. Harris
*Attorney, Agent, or Firm*—Oliff & Berridge

[57] ABSTRACT

This invention provides novel ester compounds represented by the following general formula (1):

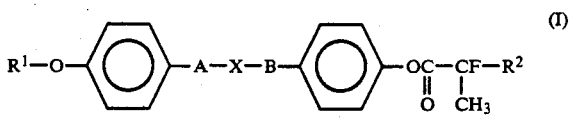

(wherein $R^1$ and $R^2$ are alkyl groups and may be the same or not, A and B are selected from a single bond and —COO—, X is selected from

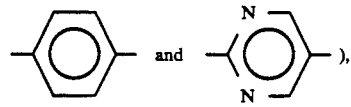

optically active bodies thereof and liquid crystal compositions containing at least one of these compounds.

12 Claims, No Drawings

ESTER COMPOUNDS AND LIQUID CRYSTAL COMPOSITIONS CONTAINING THE SAME

BACKGROUND OF THE INVENTION

1. Field of the Invention

This invention relates to novel ester compounds which can take a stable thermotropic liquid crystal state and can be utilized as a liquid crystalline material useful for use in optoelectronics related elements using a liquid crystal and electrochemichromism such as display for liquid crystal television receiver, optical printer head, opto-Fourier transform element, light valve and the like, and liquid crystal compositions containing these compounds.

2. Related Art Statement

At the present liquid crystal compounds are applied to various apparatuses as a displaying material and put to practical use in watch, personal calculator, small size television receiver and the like. These apparatuses use a cell containing a liquid crystalline material composed mainly of nematic liquid crystal and adopt a display system called as TN type or STN type. In this case, the operation of the cell is based on a weak interaction ($\Delta\epsilon E^2/2$) between dielectric anisotropy $\Delta\epsilon$ and electric field E, so that the cell has a drawback that the response time to the electric field is as slow as few tens m sec. Therefore, when the cell is applied to the television receiver, an active matrix system in which many switching elements are arranged at respective pixels is generally used as the cell driving system, which becomes an obstruct for realizing a large size display screen. However, a liquid crystal cell having a high-speed response property as $\mu$ sec order and a property not changing orientation of liquid crystal molecule even in the switching-off of the electric field (memory property) is made possible by appearance of ferroelectric liquid crystals representing 4-(4-n-decyloxybenzylideneamino) cinnamic acid-2-methylbutyl ester (DOBAMBC) synthesized by R. B. Meyer et al. in 1975 and a new displaying system using these liquid crystals as proposed by N. A. Clark (Applied Phys. Lett. 1980, 36, 899). When employing the displaying element with these materials, it is possible to realize a liquid crystal television receiver with a simple matrix system in which a multiplex driving mode is used without using the switching elements, which is fairly advantageous as compared with the active matrix system in view of productivity, cost, reliability, formation of large size display screen and the like.

Therefore, many ferroelectric liquid crystalline materials are synthesized and proposed up to the present. In order that these ferroelectric liquid crystalline materials are used as a displaying material, they are required to have some properties, among which it is fundamentally required to exhibit a smectic C phase and to have a large spontaneous polarization over a wide temperature range near room temperature and to be a chemical stability. In a greater part of the early ferroelectric liquid crystals, however, the spontaneous polarization was as small as not more than 10 nC/cm$^2$, and they were chemically unstable because Schiff's base was existent in their molecules.

Recently, there is reported the appearance of large spontaneous polarization through chemically stable ester compounds. For instance, a compound having the following formula:

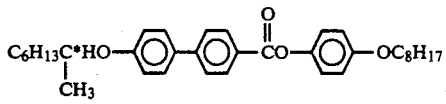

forms a liquid crystal of chiral smectic C phase over a temperature range of 78.7°~103.3° C. and of cholesteric phase over a temperature range of 103.3°~120.8° C., and the spontaneous polarization at 83° C. of this liquid crystal is 89 nC/cm$^2$ (Japanese Patent laid open No. 61-43).

On the other hand, in order to decrease the temperature range exhibiting a chiral smectic C phase, there is reported a synthesis of compounds having two rings. For instance, a biphenyl compound having the following formula:

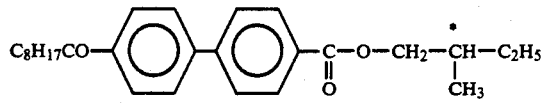

exhibits a chiral smectic C. phase at 44° C. in the cooling (Japanese Patent laid open No. 59-118644).

Furthermore, there is reported phenylpyrimidine derived compounds exhibiting a stable chiral smectic C phase near room temperature. For example, a compound having the following formula:

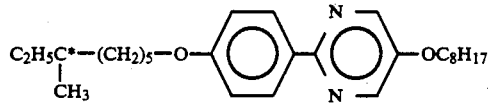

forms a liquid crystal of chiral smectic C phase over a temperature range of 40.7°~82.8° C. and of smectic A phase over a temperature range of 82.8°~89.1° C.

However, said ester compounds have a drawback that the temperature range exhibiting a chiral smectic C phase is higher. Further, said biphenyl compounds have a monotropic and unstable chiral smectic C phase. Furthermore, as to said phenylpyrimidine derived compounds, it is presumed that the response time at 43° C. of this liquid crystal is as slow as 1,500 $\mu$s and the spontaneous polarization is fairly small.

That is, in a liquid crystalline material for displaying apparatuses required to have a high-speed response property and the like, it is required to have a large spontaneous polarization and a low viscosity and to exhibit a chiral smectic C phase over a wide temperature, but it is actual circumstances that there is not yet developed a liquid crystalline material sufficiently satisfying their physical properties.

Recently, however, there are reported many compounds having a fluorine atom or a trifluoromethyl group on an asymmetric carbon in their molecule. For instance, Heppke et al. reported that a compound having a fluorine atom on an asymmetric carbon in its molecule and having the following formula:

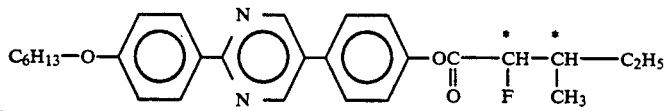

exhibits a chiral smectic C phase and a spontaneous polarization of not less than 400 nC/cm² (Proceedings of the 12th International Conference on Liquid Crystal).

In addition, there is reported a compound having a trifluoromethyl group on an asymmetric carbon in its molecule and having the following formula:

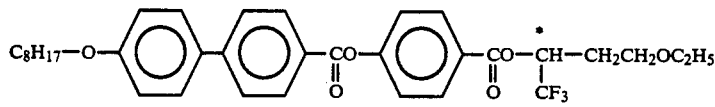

exhibits a chiral smectic C phase over a temperature range of 115.5°~93.1° C. and a spontaneous polarization of 166 nC/cm² (Japanese Patent laid open No. 64-3154).

There is anothr proposition on a derivative of 2-fluoro-2-methylbutyric acid having the following formula:

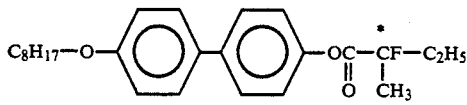

However, there is no description of any properties of the compound (Japanese Patent laid open No. 1-501394).

SUMMARY OF THE INVENTION

The inventors have made various investigations in order to more enhance the liquid crystal properties of the above proposed compounds, and found that a compound in which the asymmetric carbon has both fluorine atom and methyl group exhibits a stable chiral smectic C phase alone.

The invention is based on the above knowledge and is to provide novel ester compounds useful as a liquid crystal compound as well as liquid compositions containing these compounds.

The invention provides an ester compound represented by the following general formula (I):

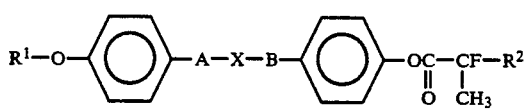

, wherein $R^1$ and $R^2$ are alkyl groups and may be the same or not, A and B are selected from a single bond and —COO—, X is selected from

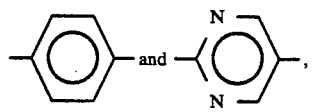

as well as a liquid crystal composition containing the above compound.

DESCRIPTION OF THE PREFERRED EMBODIMENTS

It is preferable that the alkyl groups shown by $R^1$ and $R^2$ in the above general formula (I) have a carbon number of 1-18 respectively from a viewpoint of actual production factors.

Moreover, among the above compounds, when the carbon adjacent to $R^2$, $CH_3$ and fluorine atom is an asymmetric carbon and the optical activity is introduced into the compound taking this carbon as an asymmetric center, the resulting optically active compound forms a preferred ferroelectric liquid crystal alone or in admixture with another compound.

Examples of the typical compounds shown by the above general formula (I) and their physical and chemical properties are as follows:

4-(2-fluoro-2-methylheptanoyloxy)phenyl 4'-octyloxybiphenyl-4-carboxylate

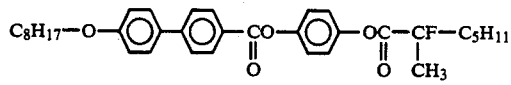

IR(KBr, cm⁻¹): 2,920, 2,850, 1,770, 1,730, 1,600, 1,500, 1,460, 1,290, 1,270, 1,180
¹H-NMR (in CDCl₃, TMS standard, δ value ppm): 8.21(d, 2H), 7.67(d, 4H), 7.27(d, 4H), 7.00(d, 2H), 4.00(t, 2H), 0.73~2.24(m, 29H)

4'-(2-fluoro-2-methylheptanoyloxy)-biphenyl 4-octyloxybenzoate

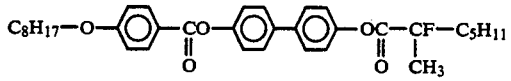

IR(KBr, cm⁻¹): 2,900, 2,850, 1,760, 1,730, 1,610, 1,490, 1,270, 1,200
¹H-NMR (in CDCl₃, TMS standard, δ value ppm): 8.20(d, 2H), 7.60(d, 4H), 7.30(d, 2H) 7.18(d, 2H), 7.00(d, 2H), 4.10(t, 2H), 0.80~2.30(m, 29H)

4-(2-fluoro-2-methylheptanoyloxy)phenyl 4-(4-octyloxyphenylcarbonyloxy)benzoate

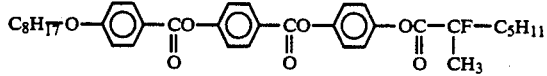

IR(KBr, CM⁻¹): 2,900, 2,850, 1,770, 1,730, 1,600, 1,500, 1,290, 1,170

¹H-NMR (in CDCl₃, TMS standard, δ value ppm): 8.24(q, 4H), 7.36(q, 6H), 7.00(d, 2H) 4.1(t, 2H), 0.80~2.20(m, 29H)

4-(2-fluoro-2-methylheptanoyloxy)-4"-hexyloxyterphenyl

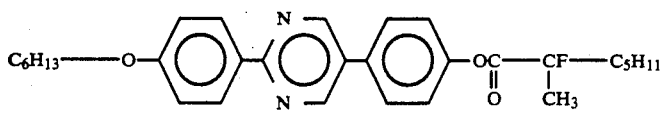

IR(KBr, CM⁻¹): 2,920, 2,850, 1,750, 1,600, 1,490, 1,240, 1,180,

¹H-NMR (in CDCl₃, TMS standard, δ value ppm): 7.8~6.8(m, 12H), 4.0(t, 2H), 0.7~2.8(m, 25H)

5-(4-(2-fluoro-2-methylheptanoyloxy)phenyl)-2-(4-hexyloxyphenyl)pyrimidine

IR(KBr, cm⁻¹): 2,920, 2,850, 1,778, 1,610, 1,580, 1,430, 1,250, 1,160

¹H-NMR (in CDCl₃, TMS standard, δ value ppm): 8.70(s, 2H), 8.50(d, 2H), 7.70(d, 2H), 7.28(s, 2H), 7.00(d, 2H), 4.10(t, 2H), 0.80~2.47(m, 25H)

5-(4-(2-fluoro-2-methylheptanoyloxy)phenyl)-2-(4-butyloxyphenyl)-pyrimidine

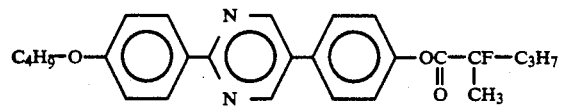

IR(KBr, cm⁻¹): 2,920, 2,850, 1,778, 1,610, 1,580, 1,430, 1,230, 1,070

¹H-NMR (in CDCl₃, TMS standard, δ value ppm): 8.94(s, 2H), 8.44(d, 2H), 7.66(d, 2H), 8.25(d, 2H), 7.00(d, 2H), 4.10(t, 2H), 0.80~2.30(m, 21H)

5-(4-(2-fluoro-2-methylpentanoyloxy)phenyl-2-(4-butyloxyphenyl)pyrimidine

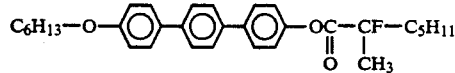

IR(KBr, cm⁻¹): 2,920, 2,850, 1,778, 1,610, 1,580, 1,430, 1,250, 1,160

¹H-NMR (in CDCl₃, TMS standard, δ value ppm): 8.80(s, 2H), 8.46(d, 2H), 7.68(d, 2H), 7.40(d, 2H), 7.00(d, 2H), 4.10(t, 2H), 0.80~2.30(m, 17H)

Moreover, the length of each carbon chain of the alkyl groups R¹ and R² shown in the formula (I) affects the temperature range forming a liquid crystal state or the physical properties such as spontaneous polarization and the like in the compound, so that it can properly be selected in accordance with the use purpose. Of course, such compound may be used alone or in admixture with the other liquid crystalline material.

The compound of the above general formula (I) according to the present invention can be obtained through the following steps.

(a) When A is single bond, B is —COO— and X is

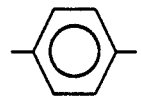

in the above general formula (I):

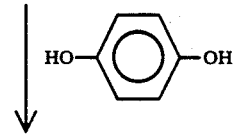

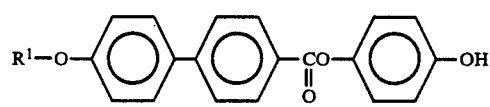

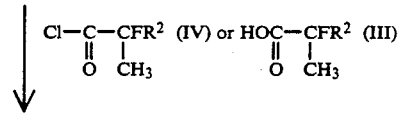

This compound can also be synthesized through the following steps.

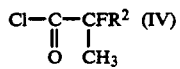

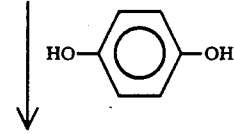

-continued

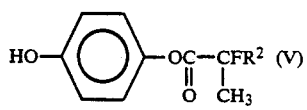

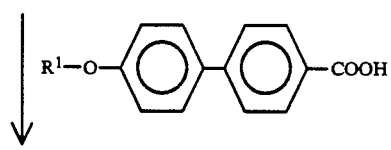

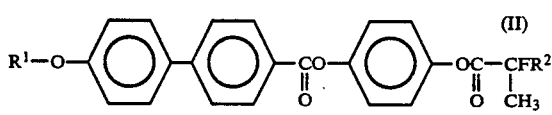

Moreover, the compounds (III) and (IV) used in the above reaction formula can be introduced from a compound (VI) in the following manner.

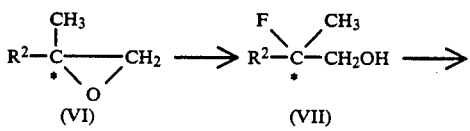

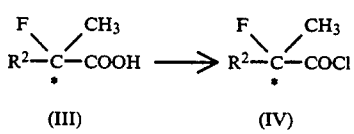

That is, 2-methyl-1,2-epoxyalkane having an optical activity (VI) is reacted with an amine-hydrogen fluoride complex or a tetrafluorosilane to obtain 2-fluoro-2-methyl-1-alkanol (VII) (Japanese Patent laid open No. 64-056058), which is oxidized with an oxidizing agent such as potassium permanganate and the like to obtain the compound (III). Moreover, the compound (III) is reacted with a chlorinating agent such as thionyl chloride and the like, whereby the compound (IV) can be obtained. In addition, the compound (V) can be synthesized in a high yield by using suitable protective groups for a hydroxyl group.

(b) When A is —COO—, B is a single bond and X is

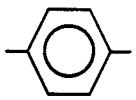

in the above general formula (I):

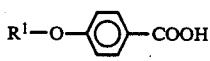

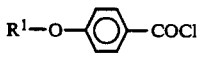

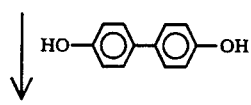

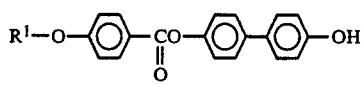

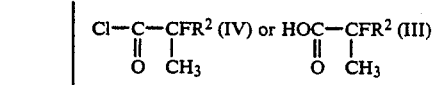

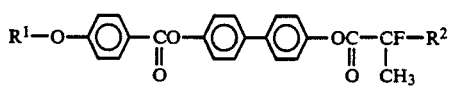

(c) When A and B are —COO— and X is

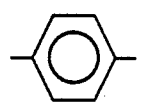

in the above general formula (I):

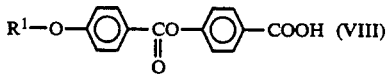

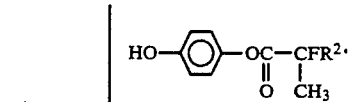

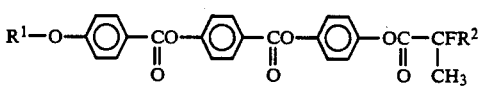

The compound of the above formula (VIII) can be obtained through the following steps.

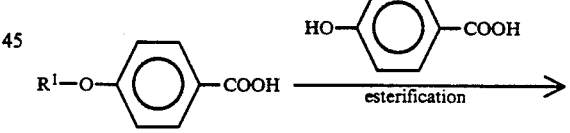

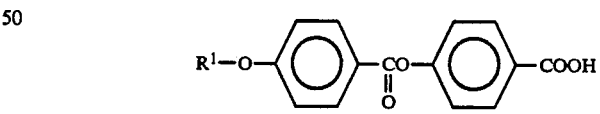

or

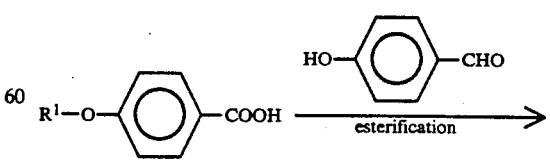

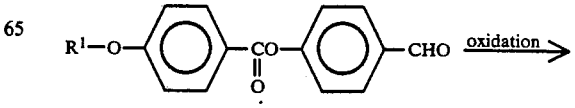

-continued

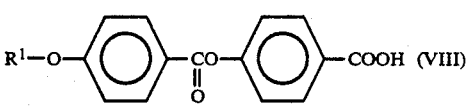

(d) When A and B are a single bond and X is

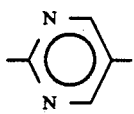

in the above formula (I):

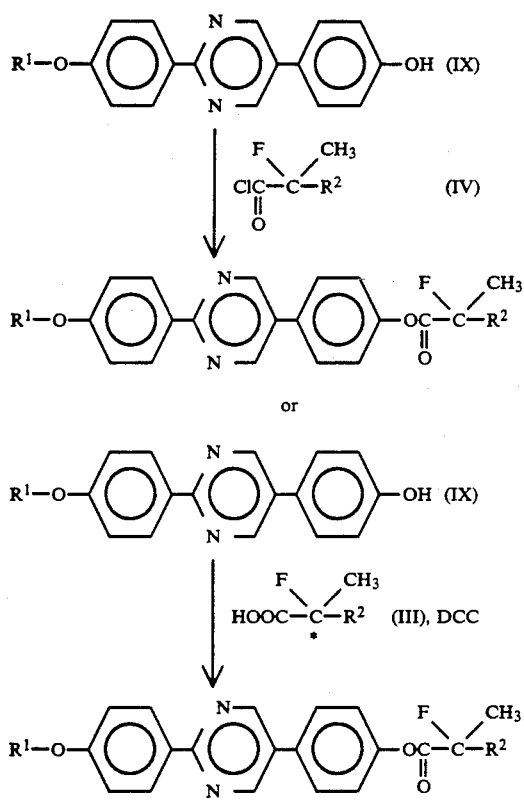

The compound (IX) can be synthesized through the following steps by referring to Journal ür Praktische Chemis. vol. 324, No. 2, 199-206 (1981).

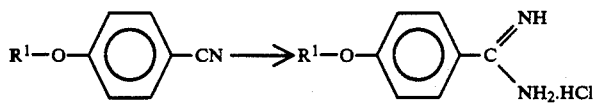
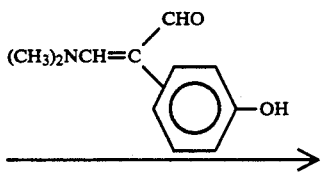
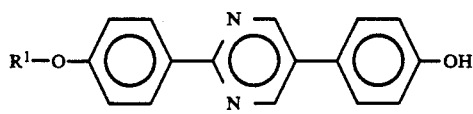

The compounds according to the invention can take a stable thermotropic liquid crystal state and form liquid crystals of ferroelectricity having a large spontaneous polarization and a short response time, so that they develop a very excellent effect as a material for optoelectronics and their related elements.

Therefore, it can be said that the compounds according to the invention are liquid crystal materials suitable for optoelectronics and their related elements utilizing liquid crystal properties or electrochemichromism, for example, a display for liquid crystal television receiver, optical printer head, opto-Fourier transform element, light valve and the like.

The following examples are given in illustration of the invention and are not intended as limitations thereof.

EXAMPLE 1

4-(2-fluoro-2-methylheptanoyloxy)phenyl 4'-octyloxybiphenyl-4-carboxylate

Synthesis of 4-(2-fluoro-2-methylheptanoyloxy)phenol 2.7 g (0.03 mol) of hydroquione and 1.5 g (8.3 mmol) of (−)-2-fluoro-2-methylheptanoyl chloride were dissolved in 25 ml of dried pyridine, which were stirred at room temperature for a night. After the completion of the reaction, the reaction mixture was placed in ethyl acetate, washed with 1 normal hydrochloric acid further with water and dried on anhydrous magnesium sulfate. After the removal of magnesium sulfate by filtration, the filtrate was purified through a column chromatography of silica gel with a developing solvent (toluene: ethyl acetate=10:1 (V/V)) to obtain 12.2 g (yield: 57%) of a white crystal.

Synthesis of 4-(2-fluoro-2-methylheptanoyloxy)phenyl 4'-octyloxybiphenyl-4-carboxylate 300 mg (1.2 mmol) of 4-(2-fluoro-2-methylheptanoyloxy)phenol obtained as aforementioned, 390 mg (1.2 mmol) of 4'octyloxybiphenyl-4-carboxylic acid, 270 mg (1.3 mmol) of N, N'-dicyclohexylcarbodiimide and 15 mg ($1.2 \times 10^{-1}$ mmol) of 4-dimethylaminopyridine were dissolved in 60 ml of dried methylene chloride, which were stirred under reflux. After the completion of the reaction, the precipitate was removed by filtration and then the filtrate was washed with 1 normal hydrochloric acid and further with water and dried on anhydrous magnesium sulfate. After the removal of magnesium sulfate by filtration, the filtrate was purified through a column chromatography of silica gel with toluene as a developing solvent and recrystallized from ethanol to obtain 140 mg (yield: 21%) of a white crystal. The thus obtained compound has the aforementioned physical and chemical properties.

Evaluation of liquid crystal properties

After the above compound was placed in a 3 μm thick cell having ITO deposited glass plates with rubbed polyimide films, the temperature of the cell was controlled on a hot stage, during which the stage of the compound in the cell was observed by means of a polarized microscope. The temperature in the hot stage varied at a rate of 2° C./min.

The compound changed from an isotropic liquid into smectic A phase at 156.0° C., into chiral smectic C phase at 127.1° C., and was crystallized at 90.0° C. during the cooling. On the other hand, it changed from the crystal into chiral smectic C phase at 104.0° C. during the heating.

In addition, the cell was applied to a triangle wave of 100 Hz and of 20 Vpp to measure the spontaneous polarization through a value of polarizing inversed current, and consequently the compound showed a spontaneous polarization of 146.2 nC/cm$^2$ at 95.7° C.

EXAMPLE 2

4'(2-fluoro-2-methylheptanoyloxy)-biphenyl 4-octyloxybenzoate

Synthesis of 4'-hydroxybiphenyl 4-octyloxybenzoate 11.2 g (0.06 mol) of p,p'-biphenol and 5.4 g (0.02 mol) of 4-octyloxybenzoyl chloride derived from 4-octyloxybenzoic acid were dissolved in 100 ml of dried pyridine, which were stirred at room temperature for a night. After the completion of the reaction, the reaction mixture was added with 6 normal hydrochloric acid to adjust pH to not more than 1 and then the precipitate was taken out by filtration. Thus obtained precipitate was recrystallized from ethanol to obtain 4.4 g (yield: 53%) of a white crystal.

Synthesis of 4'(2-fluoro-2-methylheptanoyloxy)biphenyl 4-octyloxybenzoate

The same reactions and post-treatments as in Example 1 were carried out with the use of 1.0 g (2.5 mmol) of 4'-hydroxybiphenyl 4-octyloxybenzoate obtained as aforementioned and 400 mg (2.5 mmol) of (−)-2-fluoro-2-methylheptanoic acid to obtain 550 mg (yield: 40%) of a white crystal. Thus obtained compound has the aforementioned physical and chemical properties.

Evaluation of liquid crystal properties

As a result of the same evaluation of liquid crystal properties as in Example 1, the above compound changed from an isotropic liquid into smectic A phase at 129.6° C. and into chiral smectic C phase at 113.0° C., and was crystallized at 87.5° C. during the cooling. On the other hand, it changed from the crystal into chiral smectic C phase at 108° C. during the heating.

In addition, as a result of the same measurement of the spontaneous polarization as in Example 1, the compound showed a spontaneous polarization of 175.5 nC/cm$^2$ at 88° C.

EXAMPLE 3

4-(2-fluoro-2-methylheptanoyloxy)phenyl 4-(4-octyloxyphenylcarbonyloxy)benzoate

Synthesis of 4-(4-octyloxyphenylcarbonyloxy)benzaldehyde 2.0 g (16 mmol) of 4-hydroxybenzaldehyde, 200 mg (1.6 mmol) of 4-dimthylaminopyridine and 4.1 g (16 mmol) of octyloxybenzoic acid were dissolved in 60 ml of methylene chloride. Then, 4.0 g (19 mmol) of N,N'-dicyclohexylcarbodiimide dissolved in 10 ml of dried methylene chloride was added thereto, which was stirred under reflux for ten hours. After the completion of the reaction, the precipitate was removed by filtration and then the filtrate was washed with 1 normal hydrochloric acid and further with water and dried on anhydrous magnesium sulfate. After the removal of magnesium sulfate by filtration, the filtrate was concentrated and the thus obtained residue was recrystallized from 20 ml of ethanol to obtain 4.6 g (81%) of a light yellow needle crystal.

Synthesis of 4-(4-octyloxyphenylcabonyloxy)benzoic acid 2.0 g (5.6 mmol) of 4-(4-octyloxyphenylcarbonyloxy)benzaldehyde was dissolved in 100 ml of acetone and then 900 mg (5.6 mmol) of potassium permanganate was added dropwise thereto over about 5 minutes. After the mixture was stirred at room temperature for a night, 1.0 g (9.6 mmol) of sodium bisulfite dissolved in 20 ml of water was added thereto to adjust pH to not more than 1. After the acetone was distilled off, the white precipitate was taken out by filtration and recrystallized from 60 ml of ethanol to obtain 1.8 g (yield: 85%) of a white crystal.

Synthesis of 4-(2-fluoro-2-methylheptanoyloxy)phenyl 4-(4-octyloxyphenylcarbonyloxy)benzoate The same reactions and post-treatments as in Example 1 were carried out with the use of 300 mg (0.18 mmol) of 4-(4-octyloxyphenylcarbonyloxy)benzoic acid obtained as aforementioned and 210 mg (0.81 mmol) of 4-(2-fluoro-2-methylheptanoyloxy)phenol shown in Example 1 to obtain 260 mg (yield: 53%) of a white crystal. Thus obtained compound has the aforementioned physical and chemical properties.

Evaluation of liquid crystal properties

As a result of the same evaluation of liquid crystal properties as in Example 1, the above compound changed from an isotropic liquid into smectic A phase at 141.1° C. and into chiral smectic C phase at 100.7° C., and was crystallized at 87.0° C. during the cooling. On the other hand, it changed from the crystal into smectic A phase at 103.0° C. during the heating.

In addition, as a result of the same measurement of spontaneous polarization as in Example 1, the compound showed a spontaneous polarization of 14.5 nC/cm$^2$ at 90.2° C.

EXAMPLE 4

4-(2-fluoro-2-methylheptanoyloxy)-4'''-hexyloxyterphenyl

Synthesis of 4'bromo-(4-(1-ethoxy)ethoxy)biphenyl 2.0 g (8.0 mmol) of p-bromophenylphenol and (32 mmol) of ethyl vinyl ether were dissolved in 20 ml of methylene chloride, which were stirred at room temperature for a night. After the completion of the reaction, the reaction mixture was washed with water and then purified through a column chromatography of silica gel with toluene as a developing solvent to obtain 1.9 (yield: 74%) of a white crystal.

Synthesis of 4-hydroxy-4'''-hexyloxyterphenyl

Into a flask containing 150 mg of magnesium was charged 0.5 ml of 4-hexyloxybromobenzene dissolved in 5 ml of dried tetrahydrofuran under a nitrogen gas flow through a dropping funnel, to which was added a grain of iodine to initiate the reaction. After the recognition of the reaction initiation, the remaining solution was charged thereinto from the dropping funnel and the resulting mixture was stirred at 50° C. for 3 hours. Thereafter, 1.9 g (5.9 mmol) of 4'bromo-(4-(1-ethoxy)ethoxy)biphenyl dissolved in 7 ml of dried tetrahydrofuran was added dropwise thereto, which was stirred under reflux for 15 hours. After the completion of the reaction, the reaction mixture was added to 6 normal hydrochloric acid, which was stirred for 1 hour. After the stirring, the precipitate was taken out by filtration.

Next, the precipitate was dissolved in 250 ml of methylene chloride, to which 1.9 g (26 mmol) of ethyl vinyl ether was added dropwise. The resulting mixture was stirred at room temperature for 2 hours. After the completion of the reaction, the reaction mixture was washed with water and then purified through a column chromatography of silica gel with a developing solvent (chloroform: hexane = 1:1 (V/V)) to obtain 340 mg of a white crystal.

Thereafter, this white crystal dissolved in 40 ml of tetrahydrofuran, to which was added 40 ml of 6 normal hydrochloric acid. The resulting mixture was stirred at room temperature for a night. After the completion of the reaction, the reaction mixture was extracted with chloroform and then the extract was washed with water and dried on anhydrous magnesium sulfate. After the removal of magnesium sulfate by filtration, chloroform was evaporated to obtain 270 mg (yield: 15%) of a white crystal.

Synthesis of 4-(2-fluoro-2-methylheptanoyloxy)-4''-hexyloxyterphenyl 240 mg (0.7 mmol) of 4-hydroxy-4''-hexyloxyterphenyl, 20 mg (0.7 mmol) of (−)-2-fluoro-2-methylhexanoic acid, 150 mg (0.7 mmol) of N,N'-dicyclohexylcarbodiimide and 10 mg (0.07 mmol) of 4-dimethylaminopyridine were dissolved in 100 ml of dried dichloromethane, which were stirred under reflux for 7 hours. After the completion of the reaction, the precipitate was removed by filtration and then the filtrate was washed with 1 normal hydrochloric acid and further with water, after which the organic phase was dried on anhydrous magnesium sulfate. After the removal of magnesium sulfate by filtration, the filtrate was purified through a column chromatography of silica gel with toluene as a developing solvent and recrystallized from 60 ml of ethanol to obtain 80 mg (yield: 24%) of a white crystal. The thus obtained compound has the aforementioned physical and chemical properties.

Evaluation of liquid crystal properties

As a result of the same evaluation of liquid crystal properties as in Example 1, the above compound changed from an isotropic liquid into smectic C phase at 189.2° C. and into chiral smectic C phase at 173.6° C., and was crystallized at 170.6° C. during the cooling. On the other hand, it changed from the crystal into chiral smectic C phase at 172.0° C. during the heating.

In addition, as a result of the same measurement of spontaneous polarization as in Example 1, the compound showed a spontaneous polarization of 82 nC/cm² at 171.6° C.

EXAMPLE 5

Preparation of liquid crystal composition

A feroelectric liquid crystal composition was prepared by adding a chiral compound to an achiral smectic C. liquid crystal host mixture, which consists of phenylpyrimidine derivatives.

The phase transition temperatures of this host mixture was as follows:

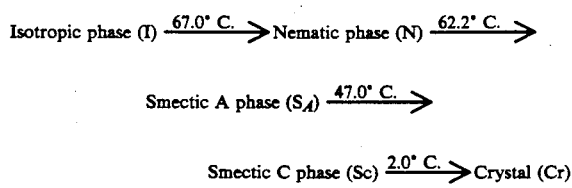

To the above host mixture 6 wt % of the compound of Example 1 having the following formula:

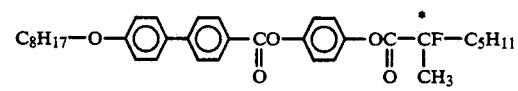

was addes as a chiral dopant. The resulting composition showed the following phase transition temperatures:

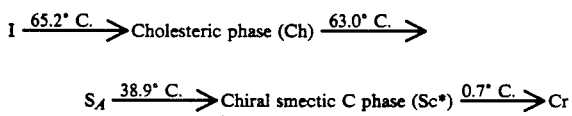

Incidentally, the same evaluation of liquid crystal properties as in Example 1 was carried out. The response time of the above composition was 960 μsec (10 Vpp/μm, 25° C.).

EXAMPLE 6

Preparation of liquid crystal composition

To the same host mixture as in Example 5 was added 6 wt % of the compound of Example 2 having the following formula:

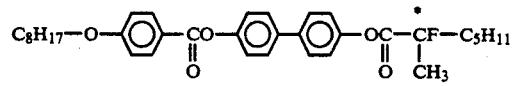

, after which the same evaluation of liquid crystal properties as in Example 1 was carried out. As a result, the composition showed the following phase transition temperatures:

The response time of the above composition was 108 μsec (10 Vpp/μm, 25° C.).

EXAMPLE 7

Preparation of liquid composition

To the same host mixture as in Example 5 was added 6 wt % of the compound of Example 4 having the following formula:

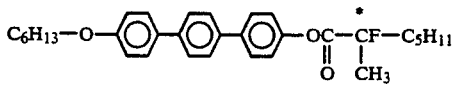

, after which the same evaluation of liquid crystal properties as in Example 1 was carried out, as a result, the composition showed the following phase transition temperatures:

The response time of the above composition was 30 μsec (10 Vpp/μm, 25° C.).

EXAMPLE 8

5-(4-(2-fluoro-2-methylheptanoyloxy)phenyl)-2-(4-hexyloxyphenyl)pyrimidine

Synthesis of 5-(4-(2-fluoro-2-metnylheptanoyloxy)phenyl)-2-(4-hexyloxyphenyl)pyrimidine 300 mg ($8.6 \times 10^{-4}$ mol) of 5-(4-hydroxyphenyl)-2-(4-hexyloxyphenyl)pyrimidine and 160 mg ($8.6 \times 10^{-4}$ mol) of (−)-2-fluoro-2-methylheptanoyl chloride were dissolved in 20 ml of dried pyridine, which were stirred at room temperature for 3 hours. After the completion of the reaction, the reaction mixture was poured into 50 ml of ethyl acetate, which was washed with 1 normal hydrochloric acid and further with water and dried on anhydrous magnesium sulfate. After the removal of magnesium sulfate by filtration, the filtrate was purified through a column chromatography of silica gel with a developing solvent (toluene: ethyl acetate=20:1 (V/V)) and recrystallized from 12 ml of ethanol to obtain 200 mg (yield: 48%) of a white crystal. The thus obtained compound has the aforementioned physical and chemical properties.

Evaluation of liquid crystal properties

As a result of the same evaluation of liquid crystal properties as in Example 1, the above compound changed from an isotropic liquid into chiral smectic C phase at 130.4° C. and further into higher ordered smectic phase which can not be identified at 83.5° C. during the cooling. On the other hand, it changed from a crystal into chiral smectic C phase at 87.8° C. during the heating.

In addition, the spontaneous polarization was measured by a triangle wave method in which a sufficient voltage was applied, and consequently the compound showed a large spontaneous polarization of 438 nC/cm² at 90.4° C.

EXAMPLE 9

5-(4-(2-fluoro-2-methylheptanoyloxy)phenyl)-2-(4-butyloxyphenyl)pyrimidine

Synthesis of 5-(4-(2-fluoro-2-methylheptanoyloxy)phenyl)-2-(4-butyloxyphenyl)pyrimidine The same procedure as in Example 8 was repeated, except that 5-(4-hydroxyphenyl)-2-(4-butyloxyphenyl)-pyrimidine was used instead of 5-(4-hydroxyphenyl)-2-(4-hexyloxyphenyl)pyrimidine, to obtain 60 mg (yield: 1%) of a white crystal. The thus obtained compound has the aforementioned physical and chemical properties.

Evaluation of liquid crystal properties

As a result of the same evaluation of liquid crystal properties as in Example 1, the above compound changed from an isotropic liquid into chiral smectic C phase at 136.5° C. and further into higher smectic phase which can not be identified at 82.2° C. during the cooling. On the other hand, it changed from a crystal into chiral smectic C phase at 90.6° C. during the heating.

In addition, the spontaneous polarization was measured by a triangle wave method in which a sufficient voltage was applied, and consequently the compound showed a large spontaneous polarization of 409.5 nC/cm² at 87.5° C.

EXAMPLE 10

Preparation of liquid crystal composition

The same host mixture as in Example 5 was used as an achiral smectic C liquid crystal composition.

To the above host mixture 6 wt% of the compound of Example 8 having the following formula:

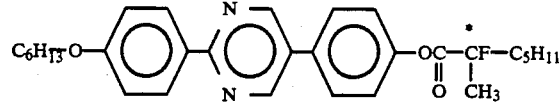

was added as a chiral dopant. The resulting composition showed the following phase transition temperatures:

Incidentally, the same evaluation of liquid crystal as in Example 1 was carried out. The cooling condition was −2° C./min.

In addition, the response time of the above composition was 59 μsec (10 Vpp/μm, 25° C.).

EXAMPLE 11

5-(4-(2-fluoro-2-methylpentanoyloxy)phenyl)-2-(4-butyloxyphenyl)-pyrimidine

Synthesis of 5-(4-(2-fluoro-2-methylpentanoyloxy)phenyl)-2-(4-butyloxyphenyl)-pyrimidine 3.6 g (0.01 mol) of 5-(4-hydroxyphenyl)-2-(4-butyloxyphenyl)pyrimidine, 1.5 g (0.01 mol) of (−)-2-fluoro-2-methylpentanoic acid, 2.1 g (0.01 mol) of N,N′-dicylohexylcarbodiimide (DCC) and 130 mg ($1.0 \times 10^{-3}$ mol) of 4-dimethylaminopyridine were dissolved in 190 ml of dried methylene chloride, which were stirred under reflux for 6 hours. After the completion of the reaction, the precipitate was removed by filtration and then the filtrate was washed with 1 normal hydrochloric acid and further with water and thereafter dried on anhydrous magnesium sulfate. After the removal of magnesium sulfate by filtration, the filtrate was purified through a column chromatography of silica gel with a developing solvent (toluene: ethyl acetate=10:1 (V/V)) and recrystallized from 30 ml of ethanol to obtain 660 mg (yield: 15%) of a white crystal. The thus obtained compound has the aforementioned physical and chemical properties.

Evaluation of liquid crystal properties

As a result of the same evaluation of liquid crystal properties as in Example 1, the above compound changed from an isotropic liquid into chiral smectic C phase at 144.6° C. and was crystallized at 120.7° C. during the cooling. On the other hand, it changed from the crystal into chiral smectic C phase at 136.8° C. during the heating.

In addition, the spontaneous polarization was measured by a triangle wave method in which a sufficient voltage was applied, and consequently the compound showed a large spontaneous polarization of 179 nC/cm$^2$ at 123.3° C.

Comparative Example

The following compound was synthesized as a comparative compound, of which the liquid crystal properties were evaluated.

4-(2-fluoro-2-methylbutanoyloxy)-4'-octyloxybiphenyl

Synthesis of
(S)-(−)-3-hydroxy-2-fluoro-2-methylpropionic acid monoethyl ester

To the 40 ml of dried methylene chloride added 3.4 ml of N,N-dimethylformamide and 8.0 ml of oxalyl chloride, which were stirred at 0° C. under a nitrogen gas flow for 1 hour. After methylene chloride was distilled off, the residue was dissolved in 30 ml of dried acetonitrile and 30 ml of dried tetrahydrofuran, to which was added dropwise 6.0 g (0.03 mol) of (S)-(−)-2-fluoro-2-methylmalonic acid monoethyl ester dissolved in 10 ml of dried tetrahydrofuran at −30° C. under a nitrogen atmosphere. The resulting mixture was stirred at −30° C. for 1 hour and thereafter cooled up to −78° C.

Next, to the above reaction solution was added dropwise 3.7 g (0.1 mol) of sodium borohydride dissolved in 30 ml of dried tetrahydrofuran at −78° C., which was stirred at −20° C. for 4 hours. Thereafter, the reaction mixture was recooled up to −78° C. and then 50 ml of 3 normal hydrochloric acid was added thereto, after which its temperature was raised to room temperature. The thus obtained mixture was extracted with ether, washed with 1 normal hydrochloric acid, 5% of sodium hydrogencarbonate and water in this order, and then dried on anhydrous magnesium sulfate. After the removal of magnesium sulfate, the filtrate was distilled under a reduced pressure to obtain 2.3 g (yield: 45%) of a colorless and transparent liquid.

Synthesis of
(S)-(−)-3-(p-toluenesulfonyl)-2-fluoro-2-methylpropionic acid monoethyl ester 2.3 g (0.02 mol) of (S)-(−)-3-hydroxy-2-fluoro-2-methylpropionic acid monoethyl ester obtained as aforementioned and 2.9 g (0.02 mol) of p-toluenesulfonyl chloride was dissolved in 20 ml of dried pyridine, which were stirred at room temperature for a night. After the completion of the reaction, 1 normal hydrochloric acid was added thereto, and then the reaction mixture was extracted with ethyl acetate, washed with 1 normal hydrochloric acid and further with water and dried on anhydrous magnesium sulfate. After the removal of magnesium sulfate by filtration, the filtrate was purified through a column chromatography of silica gel with a developing solvent (toluene: ethyl acetate=5:1 (V/V)) to obtain 3.8 g (yield: 82%) of a light yellow liquid.

Synthesis of (S)-(−)-2-fluoro-2-methylbutanoic acid monoethyl ester 4.8 g (0.025 mol) of copper iodide was added to 10 ml of dried ether, which was cooled to −25°∼−30° C. under a nitrogen gas flow and thereafter 36 ml of methyl lithium was added dropwise thereto. Then, 3.8 g (0.01 mol) of (S)-(−)-3-(p-toluenesulfonyl)-2-fluoro-2-methylpropionic acid monoethyl ester dissolved in 10 ml of dried ether at −15°∼−20° C. was added dropwise thereto, which was stirred at 0°∼5° C. for 10 hours. After the completion of the reaction, the precipitate was removed by filtration and then the filtrate was washed with 1 normal hydrochloric acid and further with water and dried on anhydrous magnesium sulfate. After the removal of magnesium sulfate by filtration, the solvent was distilled off and the residue as it is was used for the following reaction.

Synthesis of (S)-(−)-2-fluoro-2-methylbutanoic acid 950 mg (6.4×10$^{-3}$ mol) of (S)-(−)-2-fluoro-2-methylbutanoic acid monoethyl ester obtained as aforementioned was dissolved in 10 ml of acetone and 400 mg (9.6×10$^{-3}$ mol) of sodium hydroxide was added thereto, which was stirred at room temperature for 4 hours. After the completion of the reaction, 15 ml of ice water was added thereto, after which the reaction mixture was washed with ether and then the aqueous phase was added with 6 normal hydrochloric acid to adjust pH to less than 1. Thereafter, the resulting product was extracted with ether and dried on anhydrous magnesium sulfate. After the removal of magnesium sulfate by filtration, ether was distilled off to obtain 440 mg (yield: 57%) of a colorless and transparent liquid.

Synthesis of
4-(2-fluoro-2-methylbutanoyloxy)-4'-octyloxybiphenyl

The same procedure as in Example 3 was carried out with the use of 200 mg (1.6×10$^{-3}$ mol) of (S)-(−)-2-fluoro-2-methylbutanoic acid obtained as aforementioned, 500 mg (1.7×10$^{-3}$ mol) of 4-hydroxy-4'-octyloxybiphenyl, 350 mg (1.7×10$^{-3}$ mol) of N, N'-dicylohexylcarbodiimide and 20 mg of 4-dimethylaminopyridine to obtain 30 mg of a white crystal as an object compound. Thus obtained compound has the following formula and physical and chemical properties:

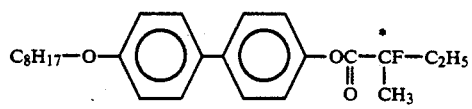

IR(KBr, cm$^{-1}$): 2,920, 2,850, 1,770, 1,610, 1,500, 1,460, 1,290, 1,230, 1,210, 1,120

$^1$H-NMR (in CDCl$_3$, TMS standard, δ value ppm): 7.67(d, 2H), 7.53(d, 2H), 7.26(d, 2H), 7.00(d, 2H), 4.00(t, 2H), 0.80~2.50(m, 23H)

Evaluation of liquid crystal properties

As a result of the same evaluation as in Example 1, the above compound changed from an isotropic liquid into smectic A phase at 77.5° C. and into higher ordered smectic phase which can not be identified at 69.4° C. during the cooling. On the other hand, it changed from a crystal into smectic A phase at 69.5° C. during the heating.

As aforementioned, it was understood that the above compound having biphenyl group as a core part did not possess a liquid crystal state of stable chiral smectic C phase.

Evaluation of liquid crystal properties as a composition

The same host mixture as in Example 5 was used as an achiral smectic C. liquid crystal composition.

As a result of the addition of 6 wt % of the above comparative compound- having the following formula:

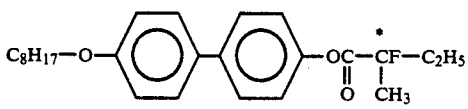

to the host mixture, the resulting composition showed the following phase transition temperatures:

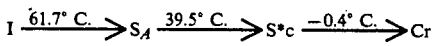

Incidentally, the same evaluation of liquid crystal properties as in Example 1 was carried out.

The response time of the above composition was 61 μsec (10 Vpp/μm, 25° C.).

However, the above comparative compound has a problem in the molecular orientation in the cell because of the disappearance of cholesteric phase (Ch), as compared with those aforementioned in the above Examples 4 and 5, so that it is not preferable. In addition to the disappearnce of the cholesteric phase, the addition of this biphenyl compound greatly lowered the smectic A to smectic C. transition temperature of the host mixture, which resulted in the ferroelectric liquid crystal composition possessing the insufficient temperature range of the chiral smectic C phase.

What is claimed is:

1. An ester compound represented by the following general formula (I):

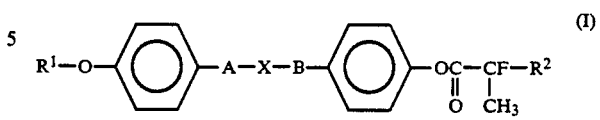

, wherein R$^1$ is a C$_1$-C$_{18}$ alkyl group and R$^2$ is a C$_1$-C$_{18}$ alkyl group and may be the same or not, A and B are selected from a single bond and —COO—, X is selected from

[benzene ring] and [pyrimidine ring].

2. The ester compound according to claim 1, wherein said compound of the general formula (I) is an optically active compound.

3. The ester compound according to claim 2, wherein said compound of the general formula (I) is 4-carboxylate-4-(2-fluoro-2-methylheptanoyloxy)phenyl 4'-octyloxybiphenyl.

4. The ester compound according to claim 2, wherein said compound of the general formula (I) is 4'-(2-fluoro-2-methylheptanoyloxy)-biphenyl 4-octyloxybenzoate.

5. The ester compound according to claim 2, wherein said compound of the general formula (I) is 4-(2-fluoro-2-methylheptanoyloxy)phenyl 4-(4-octyloxyphenylcarbonyloxy)benzoate.

6. The ester compound according to claim 2, wherein said compound of the general formula (1) is 4-(2-fluoro-2-methylheptanoyloxy)-4''-hexyloxyterphenyl.

7. The ester compound according to claim 2, wherein said compound of the general formula (I) is 5-(4-(2-fluoro-2-methylheptanoyloxy) phenyl)-2-(4-hexyloxyphenyl)pyrimidine.

8. The ester compound according to claim 2, wherein said compound of the general formula (I) is 5-(4-(2-fluoro-2-methylheptanoyloxy) phenyl)-2-(4-butyloxyphenyl)-pyrimidine.

9. The ester compound according to claim 2, wherein said compound of the general formula (I) is 5-(4-(2-fluoro-2-methylpentanoyloxy) phenyl)-2-(4-butyloxyphenyl)pyrimidine.

10. A liquid crystal composition containing at least one of the ester compounds claimed in claim 1.

11. The ester compound of claim 1, wherein R$^2$ is a C$_2$-C$_{18}$ alkyl group.

12. A liquid crystal composition containing at least one of the ester compounds claimed in claim 11.

* * * * *